United States Patent [19]

Bergersen

[11] 3,939,598

[45] Feb. 24, 1976

[54] ORTHODONTIC POSITIONER WITH OVERBITE OR OPEN BITE CORRECTING OR RELAPSE INHIBITING CAPABILITY

[76] Inventor: Earl O. Bergersen, 950 Linden Ave., Winnetka, Ill. 60093

[22] Filed: Jan. 23, 1975

[21] Appl. No.: 543,356

[52] U.S. Cl. ............................................... 32/14 B
[51] Int. Cl.² ........................................... A61C 7/00
[58] Field of Search ...... 32/14 A, 14 R, 14 B, 14 E; 128/136

[56] References Cited
UNITED STATES PATENTS

| | | | |
|---|---|---|---|
| 2,467,432 | 4/1949 | Kesling | 32/14 B |
| 3,478,742 | 11/1969 | Bohlmann | 32/14 R |
| 3,848,335 | 11/1974 | Bergersen | 32/14 B |

FOREIGN PATENTS OR APPLICATIONS 897,464 4/1972 Canada ........................ 32/14 B

*Primary Examiner*—Louis G. Mancene
*Assistant Examiner*—J. Q. Lever
*Attorney, Agent, or Firm*—Larson, Taylor and Hinds

[57] ABSTRACT

In an orthodontic tooth positioning appliance of the type wherein all teeth normally engage the isthmus of the tooth receiving troughs substantially concurrently, the thickness of the isthmus is either (a) increased at the anterior teeth, relative to the thickness at the posterior teeth, for correcting or preventing relapse of a correction for overbite or (b) decreased at the anterior teeth, relative to the thickness at the posterior teeth to correct for or prevent relapse of a correction for open bite.

14 Claims, 13 Drawing Figures

ORTHODONTIC POSITIONER WITH OVERBITE OR OPEN BITE CORRECTING OR RELAPSE INHIBITING CAPABILITY

BACKGROUND OF THE INVENTION

This Invention relates to tooth positioning appliances, and in particular it relates to an adaptation of such an appliance for the correction of or retention of a correction for overbite or open bite conditions.

In the field of orthodontics, conventional orthodontic devices such as bands or the like are often used for straightening teeth to bring them to a predetermined position of proper or close to proper occlusion. To bring the teeth into a final position of desired orientation in the mouth, the orthodontist will often use a tooth positioner. One type of positioner which is custom made for each individual patient is illustrated in the Kesling U.S. Pat. No. 2,467,432. Another type of positioner which is preformed in a limited number of sizes, and wherein the patient is fitted with the correct one of the limited number of sizes is shown in my Canadian Pat. No. 897,464, issued Apr. 11, 1972.

In the manufacture of both custom and preformed positioners, the present practice is to make the positioners so that as the teeth approach their desired position and the patient occludes his teeth into the positioner, all of the occlusal surfaces of the complete dentition tough the isthmus of the positioner substantially concurrently. A slight variation of this involves a protective feature built into the preformed positioners wherein, in order to compensate for varying free-way spaces (the space between the posterior maxillary and mandibular occlusal surfaces during a person's normal rest position) the positioners were designed such that the occlusal surfaces of the anterior teeth would tough the isthmus of the positioner one half millimeter prior to the occlusal surfaces of the posterior teeth.

While these positioners perform their intended functions satisfactorily, it has been found that they cause increases in vertical overbite, i.e. the excess downward extension of the maxillary anterior teeth over the mandibular anterior teeth, and encourage relapse of corrected overbites. This represents a significant disadvantage since overbite is the most difficult characteristic to treat orthodontically and to retain, and because overbite is probably the most important cause of periodontal degeneration in the adult dentition and cannot be successfully corrected in the adult stage. Clearly then, if overbite could be corrected and properly retained in the growing child, it would be a very significant service to the future health of that child's dentition.

Hence, there exists a need for improvements in the art relating to orthodontic positioners for effectively dealing with overbite problems.

SUMMARY OF THE INVENTION

Thus, it is a purpose of the present invention to provide an improved orthodontic positioning appliance which overcomes the above described problems in the prior art.

This purpose of the present invention is achieved by altering the estabished philosophy that all occlusal surfaces should tough at substantially the same time, and instead purposely creating premature occlusal contact of certain groups of teeth relative to other groups of teeth. This stimulates depression, i.e. movement into the gum, of the prematurely contacting teeth but not of the remaining, subsequently contacting teeth.

To correct for overbite, the thickness of the isthmus extending between the labial-buccal and lingual flanges is varied from that thickness wherein all occlusal surfaces contact substantially concurrently such that the thickness is increased in the area of the anterior teeth relative to the area of the posterior teeth on both sides so that the anterior teeth contact the isthmus first whereby a depressive force urges the anterior teeth into the gum as the patient attempts to continue to occlude his teeth until the posterior teeth in fact engage. This variation of the isthmus thickness can be accomplished either by reducing the thickness in the area of the posterior teeth or increasing the thickness in the area of the anterior teeth. However, in view of the fact that the isthmus is already quite thin in the area of the posterior teeth (for example, 1.5 mm) it might often be inadvisable to further reduce the thickness at this location so that it would be preferable to effect this variation by increasing the thickness of the isthmus at the anterior teeth. It has been found that an increase in the thickness at the anterior region relative to the posterior region as compared with the normal concurrent occlusion design would optimally be between 1 and 2 mm, thereby causing the anterior teeth to be depressed 1 to 2 mm before contact of the posterior teeth is possible. The principles of the invention are applicable for either the maxillary or the mandibular teeth and the invention can be carried out in the upper trough and/or the lower trough of a positioner having such an upper and lower trough or in the single trough of a maxillary-only or mandibular-only trough positioner.

The basic concept of the present invention can be extended to correct for open bite and/or retain a previous correction for open bite. Open bite is essentially the opposite of overbite. In this condition the maxillary anterior teeth do not extend downwardly over the front surfaces of the mandibular anterior teeth by a sufficient amount. In accordance with the present invention, such open bite can be corrected and/or a previous correction for open bite can be retained by simply reversing the variation made for overbite. In this case the thickness of the isthmus would be increased in the posterior region relative to the anterior region as compared to the thickness of the isthmus when all teeth engage the isthmus substantially concurrently. This would have the effect of exerting depressive forces on the prematurely contacting posterior teeth as the patient attempts to continue occluding the anterior teeth after initial occluding engagement of the posterior teeth. The effect of successful depression of the posterior teeth would of course be that the maxillary anterior teeth could then move farther down over the mandibular anterior teeth before occlusion of the posterior teeth, thereby effecting a correction of open bite. As with the overbite correction, the increase in thickness would optimally cause a premature contacting (in this case of the posterior teeth) of between 1 and 2 mm. In all other respects, the features described above with respect to overbite correction would apply as well to open bite correction.

Thus, it is a purpose of the present invention to provide a new and improved orthodontic positioner which will either correct for or prevent a relapse of a previous correction for overbite and/or open bite.

It is still another object of this invention to provide an orthodontic positioner of the type described in which the thickness of the isthmus is varied from the thickness at which all teeth would occlude substantially concurrently such that the anterior teeth engage prior to the posterior teeth for exerting a depressive force against the anterior teeth so as to correct for and/or prevent a relapse of a previous correction for overbite.

It is still another object of this invention to provide an orthodontic positioner wherein the thickness of the isthmus is varied from that thickness at which all teeth would occlude substantially concurrently such that the thickness is increased in the area of the posterior teeth relative to the thickness in the area of the anterior teeth so that the posterior teeth will contact the isthmus prior to the anterior teeth, to thereby cause a depressive force against the posterior teeth to thus correct or prevent a relapse of a previous correction for open bite.

These and other objects of the present invention will become apparent from the detailed description to follow, together with the accompanying drawings.

BRIEF DESCRIPTION OF THE DRAWINGS

There follows a detailed description of preferred embodiments of the present invention which are to be read together with the accompanying drawings which are provided solely for purposes of illustration and wherein.

DETAILED DESCRIPTION OF THE PREFERRED EMBODIMENTS

Referring now to the figures, like elements represent like numerals through out the several views.

Figure 1:
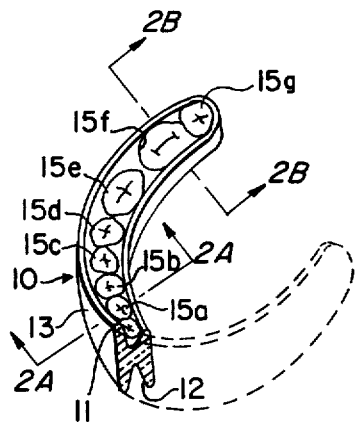
FIG. 1 is a perspective view, partially in full outline and partially in dotted outline showing an orthodontic positioner of the type with which the present invention is concerned.

Referring to FIG. 1, the positioner as shown herein includes an upper trough 11 for receiving the maxillary teeth and a lower trough 12 for receiving the mandibular teeth. The troughs are formed generally by labial-buccal flange 13 and lingual flange 14, these flanges being connected by an isthmus portion which interconnects the same. Both the upper and lower troughs are provided with tooth receiving depressions or sockets, the upper sockets being designated 15a through 15g from the right central incisor through to the last molar, respectively. The lower teeth, where visible are designated as 16 and carry the corresponding subscript a through g. Reference may be had to above mentioned patents for further details of either the custom or the preformed positioner.

Figure 2A:
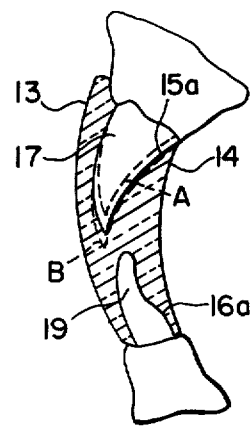
FIG. 2A is an enlarged sectional view taken along line 2A—2A of FIG. 1 and showing the central incisor teeth of a human mouth in place in the positioner.
Figure 2B:
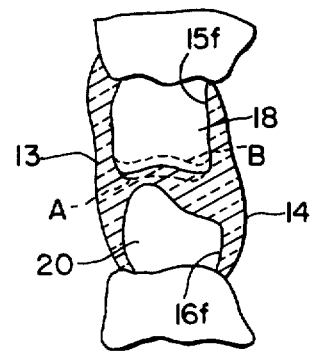
FIG. 2B is an enlarged sectional view taken along line 2B—2B of FIG. 1 and showing molars of a human mouth in place within the positioner.
Figure 3A:
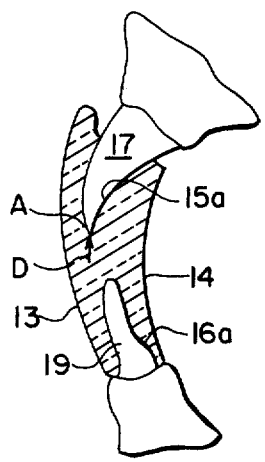
FIGS. 3A and 3B are sectional views similar to FIGS. 2A and 2B, respectively, and showing the adaptation of the positioner for treating overbite.
Figure 3B:
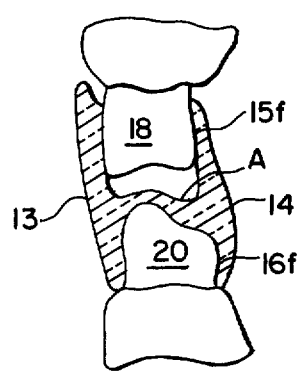

FIGS. 2A and 2B as well as FIGS. 3A and 3B illustrates the adaptation of the positioner of FIG. 1 to correct for overbite and/or prevent relapse of a previous correction for overbite. As illustrated in solid lines in FIGS. 1, 2A and 2B, the positioner is of the previous construction whereby all teeth contact the positioner substantially concurrently upon occlusion of the teeth. However, to correct for overbite, it is desirable that the anterior teeth engage the isthmus before the posterior teeth. This modification can be effected by either making the isthmus thicker in the area of the anterior teeth, making it thinner in the area of the posterior teeth or effecting any combination of these. These two modifications are shown in the dotted lines referred to by the letter A in FIGS. 2A and 2B. FIGS. 3A and 3B then illustrate the positioner of FIGS. 1, 2A and 2B with the modified isthmus according to the dotted lines A of FIGS. 2A and 2B. FIGS. 3A and 3B are now intended to represent the position of the teeth at the same point in time, namely that point during occlusion when the edge of the central incisor 17 engages the isthmus in depression 15a. In this particular embodiment the lower depressions have not been changed so that at the point illustrated in FIGS. 3A and 3B, the illustrated lower teeth 19 and 20 will have moved completely into their respective depressions and only the posterior maxillary teeth will have failed to contact the isthmus in their respective sockets as shown for the tooth 18 in FIG. 3B. As the patient attempts to complete occlusion of the posterior teeth, the incisal edge of tooth 17 will simply react against the isthmus in depression 15a causing an upward depression force indicated by the arrow D tending to urge the tooth 17 into the gum.

Figure 4A:
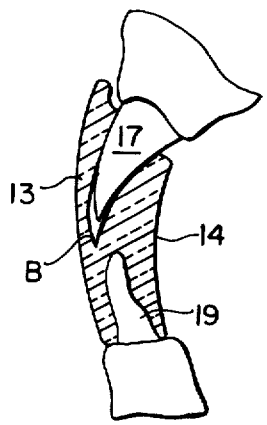
FIGS. 4A and 4B are sectional views similar to FIGS. 2A and 2B but showing the adaptation of the positioner for treating open bite.
Figure 4B:
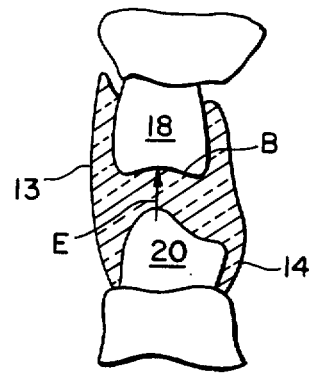

To illustrate the modification to correct for open bite references made to FIGS. 2A, 2B, 4A and 4B. In this case the positioner of FIGS. 1, 2A and 2B is modified so as to increase the thickness of the isthmus at the posterior teeth or decrease the thickness of the isthmus at the anterior teeth, or any combination thereof, such that the posterior teeth contact the isthmus before the anterior teeth. These possible combinations are shown by the dotted lines B in FIGS. 2A and 2B. FIGS. 4A and 4B illustrate the positioner of FIG. 1 modified according to both of these dotted lines B of FIGS. 2A and 2B. As in the case of FIGS. 3A and 3B, FIGS. 4A and 4B illustrate a common point in time in the occlusion of teeth. As is evident from FIGS. 4A and 4B, a point is reached at which the maxillary molar 18 has moved into its socket, as have all of the lower teeth as represented by the teeth 19 and 20 in figures. However, the maxillary anterior teeth, as represented by the tooth 17 have not yet reached the bottom of their respective sockets. Hence, as the patient attempts to complete the occlusion to move the anterior maxillary teeth to the bottom of their respective sockets, the isthmus below the maxillary posterior teeth, as presented by the tooth 18, will react against the isthmus, causing an upward depressive force represented by the arrow E, tending to urge the posterior teeth up into the gum.

In the description of the invention with respect to FIGS. 1 through 4, there has been illustrated a positioner having both an upper trough and a lower trough for receiving both the maxillary and mandibular teeth. Further, in this illustrated embodiment, the modification of the present invention has been made only with respect to the upper teeth. However, the principles of the present invention are equally applicable to the lower teeth. Hence, in practice the above described modification of the basic positioner could be made to the lower portion of the positioner either in combination with a modification to the upper portion or completely in lieu thereof, i.e. for purposes of effecting selective depressive forces on only the lower teeth. Since the application of the present invention to the lower teeth would be the same in principle as applied to the lower teeth but simply the reverse thereof, a detailed description of this type of modification has been omitted for purposes of brevity.

Figure 5:
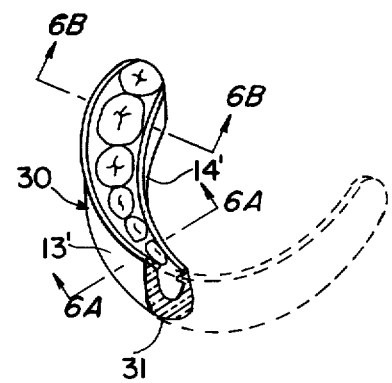
FIG. 5 is a perspective view similar to FIG. 1 but showing an orthodontic positioner for use with the maxillary teeth only.
Figure 6A:
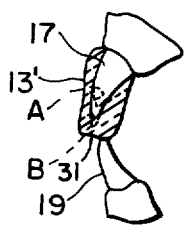
FIG. 6A is a sectional view taken along line 6A—6A of FIG. 5, and showing the central incisor teeth in place relative to the positioner.
Figure 6B:
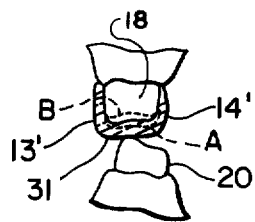
FIG. 6B is a sectional view taken along line 6B—6B of FIG. 5 and showing the molars of a human mouth in place with respect to the positioner.

The present invention is also applicable to positioners having only an upper trough or only a lower trough. A positioner having only an upper trough is shown in FIG. 5 and sectional views 6A and 6B. The positioner 30 shown therein includes an upper trough and an isthmus formed between labial-buccal flange 13' and lingual flange 14', and the sockets shown therein are similar to the sockets 15 in FIG. 1. In this case, in place of a lowr trough, the bottom of the isthmus is defined by a lower edge 31. FIGS. 6A and 6B illustrate the two dotted lines A, either of which or any combination of which could be utilized to modify the isthmus to correct for overbite or prevent a relapse of a previous overite correction in precisely the same manner as described above with respect to FIGS. 3A and 3B, and the dotted lines B represent modification lines for correcting for open bite or preventing relapse of a previous open bite correction in precisely the same manner as illustrated and described above with respect to FIGS. 4A and 4B.

Figure 7:
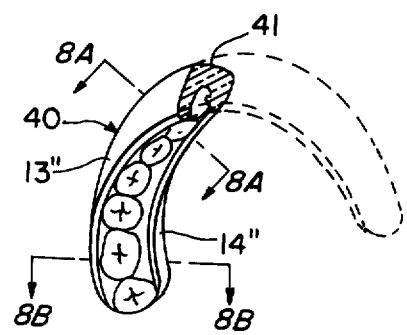
FIG. 7 is a perspective view similar to FIG. 1 but showing a positioner for use only with the mandibular teeth.
Figure 8A:
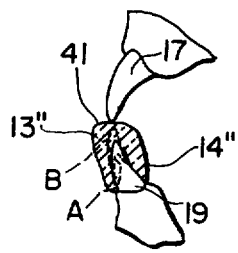
FIG. 8A is a sectional view taken along 8A—8A of FIG. 7 and showing the central incisor teeth of a human mouth in place with respect to the positioner.
Figure 8B:
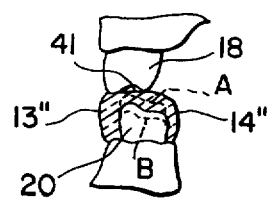
FIG. 8B is a cross-sectional view taken along 8B—8B of FIG. 7 and showing the molars of a human mouth in place with respect to the positioner.

FIGS. 7, 8A and 8B illustrate a mandibular positioner 40 having a lower trough and an isthmus formed between labial-buccal flange 13'' and a lingual flange 14'' and forming an upper edge 41. This positioner is similar in all respects but of course the reverse of that shown in FIGS. 5, 6A and 6B. As in those figures, the dotted lines A represent modifications for treating overbite and the dotted lines B represent modifications for treating for open bite.

Although the invention has been described in considerable detail with respect to preferred embodiments thereof, it will be apparent that the invention is capable of numerous modifications and variations apparent to those skilled in the art, without departing from the spirit and scope of the invention, as defined in the claims.

I claim:

1. An orthodontic tooth positioning appliance which is generally U-shaped in plan view and which includes at least one tooth receiving trough of a size and shape for positioning at least one row of a patient's upper and lower row of teeth, said trough being defined by lingual and labial-buccal flanges and including an isthmus interconnecting said flanges, the thickness of the isthmus being such that as the side thereof opposite the trough rests against the occlusal surfaces of the row other than said one row, the anterior teeth of said one row engage the isthmus before the posterior teeth of said one row to exert a force against the anterior teeth depressing them into the gum to correct for overbite or to retain a previous overbite correction as the posterior teeth complete their movement towards engagement with the isthmus.

2. An orthodontic appliance according to claim 1, in which the thickness of the isthmus at the anterior teeth is one to two millimeters greater than the thickness would be for the anterior and posterior teeth of said row to engage the isthmus concurrently.

3. An orthodontic appliance according to claim 1, wherein the appliance includes only a single trough for treating the maxillary teeth.

4. An orthodontic appliance according to claim 1, wherein the appliance includes only a single trough for treating the mandibular teeth.

5. An orthodontic appliance according to claim 1, wherein the appliance includes both an upper trough and a lower trough for receiving both the maxillary teeth and the mandibular teeth.

6. An orthodontic appliance according to claim 1, wherein the appliance is a preformed appliance constructed for fitting a plurality of different patients within a given size range.

7. An orthodontic appliance according to claim 1, wherein the appliance is a custom made appliance, custom made for a specific patient.

8. An orthodontic tooth positioning appliance which is generally U-shaped in plan view and which includes at least one tooth receiving trough of a size and shape for positioning at least one row of a patient's upper and lower row of teeth, said trough being defined by lingual and labial-buccal flanges and having an isthmus interconnecting said flanges, the thickness of the isthmus being such that as the side thereof opposite the trough rests against the occlusal surfaces of the row other than said one row, the posterior teeth of said one row engage th isthmus before the anterior teeth of said one row to exert a force against the posterior teeth depressing them into the gum to correct for open bite or to retain a previous open bite correction as the anterior teeth complete their movement towards engagement with the isthmus.

9. An orthodontic appliance according to claim 8, in which the thickness of the isthmus at the posterior teeth is 1 to 2 millimeters greater than the thickness would be for the anterior and posterior teeth of said row to engage the isthmus concurrently.

10. An orthodontic appliance according to claim 8, wherein the appliance includes only a single trough for treating the maxillary teeth.

11. An orthodontic appliance according to claim 8, wherein the appliance includes only a single trough for treating the mandibular teeth.

12. An orthodontic appliance according to claim 8, wherein the appliance includes both an upper trough and a lower trough for receiving both the maxillary teeth and the mandibular teeth.

13. An orthodontic appliance according to claim 8, wherein the appliance is a preformed appliance constructed for fitting a plurality of different patients within a given size range.

14. An orthodontic appliance according to claim 8, wherein the appliance is a custom made appliance, custom made for a specific patient.

* * * * *